United States Patent [19]
Assaraf et al.

[11] Patent Number: 5,455,161
[45] Date of Patent: Oct. 3, 1995

[54] METHOD FOR THE MONITORING OF MULTIPLE ANTICANCER DRUG RESISTANCE

[75] Inventors: Yehuda G. Assaraf, Nesher; Uriel Bachrach, Jerusalem, both of Israel

[73] Assignee: Technicon Reseach & Development Foundation Ltd., Technicon City, Israel

[21] Appl. No.: 95,141

[22] Filed: Jul. 20, 1993

[30] Foreign Application Priority Data

Jul. 23, 1992 [IL] Israel ......................................... 102617

[51] Int. Cl.$^6$ ...................... G01N 33/574; G01N 33/573; G01N 33/53

[52] U.S. Cl. .......................... 435/7.23; 435/7.4; 435/7.9; 435/7.92; 435/4; 435/29; 435/39; 435/183; 435/18

[58] Field of Search ................................ 435/7.23, 4, 18, 435/29, 39, 7.4, 7.9, 7.92, 183

OTHER PUBLICATIONS

Chang, B. K., et al., *Cancer Research* 44, 5100–5104, Nov. 1984.
Quemener, V., et al., *Anticancer Res.*, 12 (6A), 1791, 1992. Abstract only.
Alhonen–Hongisto, L., et al., *Biochem. Biophys. Res. Comm.*, 144(1), 132–137, 1987.
T. Kuroki, Colony Formation of Mammalian Cells on Agar Plates and its Application to Lederberg's Replica Plating, *Experimental Cell Research* 80 (1973), pp. 55–62.
Thomas E. Moon, Quantitative and Statistical Analysis of the Association Between In Vitro and In Vivo Studies, *Progress in Clinical and Biological Research*, vol. 48, 1980, pp. 209–221.
Sydney E. Salmon et al, Clinical Correlations of In Vitro Drug Sensitivity, *Progress in Clinical and Biological Reseach*, vol. 48, 1980, pp. 223–245.
Yehuda G. Assaraf et al, Determination of Multidrug Resistance Levels in Cultured Mammalian Cells Using Ornithine Decarboxylase Activity, *Analytical Biochemistry*, 216, pp. 97–108 (1994).

Michael C. Alley et al, Feasibility of Drug Screening with Panels of Human Tumor Cell Lines Using a Microculture Tetrazolium Assay, *Cancer Research* 48, pp. 589–601, Feb. 1, 1988.
Harry K. Slocum et al, An Enzymatic Method for the Disaggregation of Human Solid Tumors for Studies of Clonogenicity and Biochemical Determinants of Drug Action, *Progress in Clinical and Biological Research*, vol. 48, pp. 339–343 (1980).
Barbara K. Chang, Differential Sensitivity of Pancreatic Adenocarcinima Cell Lines to Chemotherapeutic Agents in Culture, *Cancer Treatment Reports*, vol. 67, No. 4, pp. 327–412, Apr. 1993.
Pekka Leinonen et al, Human Myeloma Cells Acquire Resistance to Difluoromethylornithine by Amplification of Ornithine Decarboxylase Gene, *The Biochemical Journal*, vol. 242, pp. 199–203 (1987).
Uriel Bachrach et al, Polyamines and Protein Kinase I. Induction of Ornithine Decarboxylase and Activation of Protein Kinase in Rat Glioma Cells, *Life Sciences*, vol. 22, pp. 817–822 (1978).

*Primary Examiner*—Toni R. Scheiner
*Attorney, Agent, or Firm*—Morgan & Finnegan

[57] ABSTRACT

The invention relates to a method for assessing clinical activity and resistance to multiple anticancer drugs of mammalian cells, based on a dose-dependent inhibition with cytotoxic agents of the cellular rise in ornithine decarboxylase activity, following serum stimulation, which comprises the steps of: (a) determining by an immunological technique the rise in the ornithine decarboxylase protein levels, after adding serum containing medium to quiescent mammalian cells, and (b) obtaining the levels of the anticancer drug resistance from the ratio of 50% inhibitory concentration of ornithine decarboxylase obtained with an anticancer drug for drug resistant cells and drug sensitive cells. The immunological technique is selected from ELISA, radioimmunoassay, immunofluorescence, flow cytometry and fluorescence microscopy. The increase in the ornithine decarboxylase activity results from an increase in the number of ornithine decarboxylase molecules.

13 Claims, 12 Drawing Sheets

METHOD FOR THE MONITORING OF MULTIPLE ANTICANCER DRUG RESISTANCE

The present invention relates to an assay for the identification and determination of drug sensitivity. More particularly, the invention relates to an assay in-vitro for the identification and determination of multidrug resistance levels to various anticancer drugs in mammalian cells.

BACKGROUND OF THE INVENTION.

As known there is an intense research and concentrated efforts towards the screening and discovery of new anticancer agents. This research relates to a wide range of malignancies, including central nervous system, colon, lung, melanoma, renal, ovarian and leukemia.

The clinical testing of primary tumor sensitivity and determination of drug dosage to be administered to individual cancer patients should maximize the elimination of malignant cells and would be useful in avoiding undesired toxic side effects exerted on healthy cells.

To-day, chemotherapy is still considered to have a main role in the treatment of a variety of human neoplasms. However,inherent and acquired anticancer drug resistance, are major obstacles towards a curative cancer chemotherapy. Thus, for example, the exposure of malignant cells or tumor cell lines to a single hydrophobic cytotoxic agent of natural origin, including: vinca alkaloids, anthracycline, epidophyllotoxins, actinomycin D, colchicine and taxol, frequently results in the emergence of cell populations exhibiting resistance to the selecting agent as well as to the remaining pleiotropic drugs that are structurally unrelated lipophilic antibiotics. This phenomenon, known as term multidrug resistance is gaining a great deal of interest. It appears, that this is a result of the overproduction of P-glycoprotein (P-170) which is an integral component of the mammalian plasma membrane. This membrane functions as an energy-dependent efflux transporter of some antitumor agents known as pleiotropic drugs. Increased P-170 expression has been detected in both normal tissues,including adrenal glands, kidney, lung, liver, colon and placenta as well as in a number of hematological malignancies including acute myeloid leukemia, multiple myeloma and non-Hodgkin's lymphoma and in untreated and treated breast cancer.

Taxol has shown very promising activity against ovarian cancer, advanced breast cancer, and other tumor types and has also been approved as an investigational drug by the F.D.A. However, the disadvantages as mentioned above for the cytotoxic agents, should be taken in account.

Several methods are used for the in-vitro assessment of antitumor drug sensitivity. These methods are based either on the colony-forming ability of cells (so called clonogenic) on cellular growth inhibition, or on cell proliferation. The widely used clonogenic cytotoxic assay was applied to non-adherent malignant cells by utilizing a soft agar-based colony formation technique. The clonogenicity-independent methods include a cell counting, after trypan blue exclusion, or using a radioactive nucleic acid precursor, for example, tritiated thymidine.

A microtiter assay based on cellular proliferation was specially developed for the assessment of anticancer drug sensitivity of mammalian cells that bear poor plating efficiencies. High-flux in-vitro antitumor drug screening methods that evaluate cell viability include the well-known colorimetric assay based on tetrazolium. According to this method, hydrogen acceptor reagent such as MTT [3,(4,5-dimethylthiazol-2-yl)] and its derivatives, when are present in viable cells become metabolically reduced, thus precipitating as insoluble coloured formazans, which are subsequently dissolved and determined by a spectrophotometer. However, clonogenic assays suffer from a number of disadvantages, the major one being the very low plating efficiency of tumor-derived cells as well as their tendency to form cell clumps. These limitations result in unreliable drug survival curves. Cellular viability assessed by colorimetric assays, such as the metabolic reduction of soluble tetrazolium salt derivatives to insoluble formazans, has several limitations including major variabilities in formazan formation between different cell lines, variabilities that result from cell culture age as well as from differences in glucose concentration at the time of assay, i.e. at the metabolic reduction of the tetrazolium salts. In order to obviate this disadvantage,it was suggested that an optimal tetrazolium concentration as well as an optimal incubation time, should be established for each cell line. However, this prior optimization of the assay conditions for each cell line, further complicates the existent terazolium-based technique.

A general disadvantage of all known methods for the in-vitro assesment of antitumor drug sensitivity, is the relatively long time involved in the obtaining some results,a factor which generally might be quite critical. The above brief review, illustrates some of the problems which exist for assays which are capable of evaluating in-vitro cell viability following exposure to anticancer drugs. Therefore, it is a long felt need for development of a reliable, rapid and versatile in-vitro assay for determining of cellular sensitivity and of multidrug resistance to antineoplastic agents in mammalian cells.

It is an object of the present invention to provide a simple method in-vitro for the identification and determination of multidrug resistance to various anticancer drugs in mammalian cells. It is another object of the present invention to provide a simple method in-vitro for the evaluating the effectiveness of certain chemotherapeutic regimens. It is yet another object of the present invention to provide a simple method in-vitro for the determination of multidrug resistance to various anti-cancer drugs in mammalian cells which is characterized by its reproducibility. It is a further object of the present invention to provide a simple method in-vitro for the determination of multidrug resistance to various anti-cancer drugs in mammalian cells which is characterized by its rapidity.

BRIEF DESCRIPTION OF THE INVENTION

The invention relates to a method for assessing clinical sensitivity and resistance to multiple anticancer drugs of mammalian cells, based on a dose-dependent inhibition with cytotoxic agents of the cellular rise in ornithine decarboxylase activity,following serum stimulation, which comprises the steps of: (a) determining by an immunological technique the rise in the content of ornithine decarboxylase protein levels, after adding serum-containing medium to quiescent mammalian cells, and (b) obtaining the levels of the anticancer drug resistance from the ratio of 50% inhibitory concentration of ornithine decarboxylase obtained with anticancer drug resistant cells and drug sensitive cells. The invention is based on the discovery that ornithine decarboxylase activity possesses the ability of an early enzymatic growth marker and thus could serve as a quantitative and diagnostic tool in monitoring cellular sensitivity or resistance to anti-cancer cancer agents. The method is characterized by a number of advantageous features which are in particular required for this determination, such as reliability, sensitivity, reproducibility, independency of clonogenicity, rapidity and simplicity.

DETAILED DESCRIPTION OF THE INVENTION AND FIGURES

A particular characteristic property of ornithine decarboxylase which was discovered according to the present invention, is its strikingly short turnover time in mammalian cells which is in the order of minutes and generally about 15 minutes, whereby its activity rapidly rises in-vitro in response to a variety of growth stimuli. Among the most effective stimuli the following can be mentioned: hormones, such as growth hormones, corticosteroids and androgens; growth factors, such as eidermal growth factor as well as the addition of fresh serum-containing medium. Other reagents required are polyamines, which are the biosynthetic products of ornithine decarboxylase, being used for optimal growth of mammalian cells. It was surprisingly found by the inventors that the ornithine decarboxylase activity and its inhibition with cytotoxic agents could reflect sensitivity of parental cells or drug resistance of cells bearing a multidrug resistance phenotype. The results show that with parental AA8 cells, quiescent Chinese hamster ovary multidrug cells respond to the addition of fresh serum-containing medium in a similar qualitative and quantitative manner regarding ornithine decarboxylase activity.

There are cases, such as with some particular malignant cells, when an optimal enzymatic activity is not achieved. In these cases, an optimization of the reaction conditions may be carried out by an increase in the volume of the crude cytoxolic extract. In this manner, the activity of the ornithine decarboxylase which will be measured is significantly increased.

It was found that wild type AA8 cells and multidrug resistant T19 cells, exhibit a rapid response to the addition of fresh medium, being characterized by a marked and reproducible increase in the ornithine decarboxylase activity. It was also found that the kinetic properties of ornithine decarboxylase from multidrug resistance of T19 cells are similar to those of ornithine decarboxylase activity from cells AA8. Based on these findings, it was concluded that ornithine decarboxylase activity does reflect the cellular sensitivity and thus the resistance to cytotoxic agents.

The assay used for determining cell extracts and ornithine decarboxylase activity was as follows:

Monolayer cells grown in the absence and presence of a known cytotoxic agent, were washed twice with 10 mls of phosphate-buffered saline and suspended in a petri dish (0.5 ml/10 cm) in an ice-cold ornithine decarboxylase buffer containing 50 mM of Tris-Cl, pH=7.3, 0.1 mM ethylene diamine tetraacetic acid, 50 uM pyridoxal 5'-phosphate (Sigma) and 5 mM of dithiothreitol. The cells were lysed under three cycles of freezing in liquid nitrogen and thawing at 37° C. The cell lysates were then centrifuged at 15,000 g for 15 minutes at 4° C., the supernatant liquid was collected and used in the assay for the ornithine decarboxylase activity. The assay was based on the Djurhuss method that utilizes a strong cation-exchange paper (Anal. Biochem. 113:352–5, 1981). The reaction mixture of (0.1 ml) in ornithine decarboxylase buffer with 50 uM of non-isotopic L-ornithine, 43 nM of (0.2uCi of L-[2,3-$^3$H] ornithine, specific activity 46.5 Ci/mmol, radioactive concentration 1mCi/ml, New England Nuclear) and 80 ul of crude cytoxolic cell extract. After incubation for 60 minutes at 37° C. under agitation, the reaction mixture was spotted onto a strip of P81 cellulose phosphate paper and dried. After washing in a solution of 0.1M ammonium hydroxide and drying, liquid scintillation counting was performed. In similar manner, blank values were determined by using 80 ul of ornithine decarboxylase buffer, instead of the cytosolic cell extract.

The protein determinations were carried out according to the method of Bradford (Anal.Biochem. 72, 248–54, 1976), using lysozyme, triple crystallization and dialysis, as a standard.

The kinetic properties of ornithine decarboxylase derived from T19 multidrug resistance cells and their wild type parental AA8 cells were examined. The apparent Michaelis constants of ornithine decarboxylase from AA8 and from multidrug resistance T19 cells for L-ornithine were 48 uM and 46 uM, respectively. However, the mean specific activities of ornithine decarboxylase from AA8 and T19 cells were 154 pmoles $CO_2$/hour/$10^6$ cells and 80 pmoles $CO_2$/h per $10^6$ cells respectively. Thus, the affinity of ornithine decarboxylase derived from AA8 and T19 cells for the substrate L-ornithine was substantially identical whereas the specific ornithine decarboxylase activity in T19 cells was 2-fold lower than in their parental AA8 cells.

Significant changes in the activity of ornithine decarboxylase were found after the addition of fresh growth medium containing 5% of fetal calf serum. After 6 hours of serum stimulation, an increase of 8.5-fold occurred, while in cultures which did not contained the fresh medium, only traces of enzyme levels were detected. This increase was found to prevail during the entire study, the peak thereof being after 36 hours from the addition of said medium. In a similar manner, there were tested the effects of addition of fresh medium to multidrug resistant T19 cell cultures and parental AA8 cells.

Figure 1:
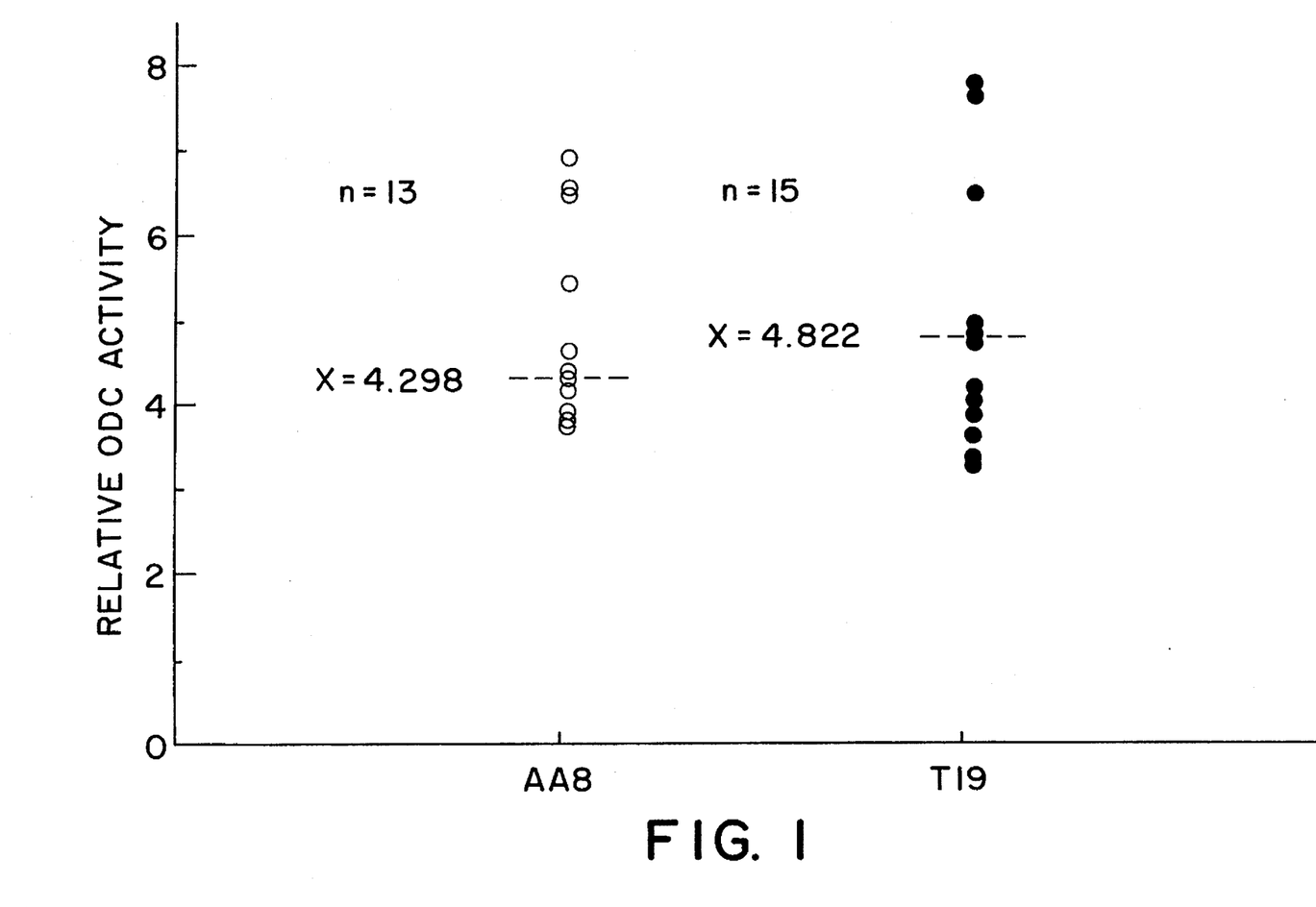
FIG. 1, shows the extent of ornithine decarboxylase activity increase in parental AA8 cells and in their multidrug resistance T19 subline following the addition of fresh serum-containing medium.

The results obtained are illustrated in FIG. 1, where the relative ornithine decarboxylase activity is correlated versus the AA8 cells and multidrug resistant T19 cells. The mean activity of ornithine decarboxylase performed with AA8 cells that received the fresh medium was 240 (S.E.) pmoles $CO_2$/hr/10 cm petri dish, while in the AA8 cells that did not receive the fresh medium the mean activity was only 55 pmoles $CO_2$/hr/10, cm petri dish. Similarly, ornithine decarboxylase activity in multidrug resistance T19 cells which received the fresh medium show a mean ornithine decarboxylase activity of 252 pmoles $CO_2$/hr/10 cm petri dish, while in the tested T19 cells which did not receive said fresh medium, the mean activity was only 50 pmoles $CO_2$/hr/10 cm petri dish.

Figure 2:
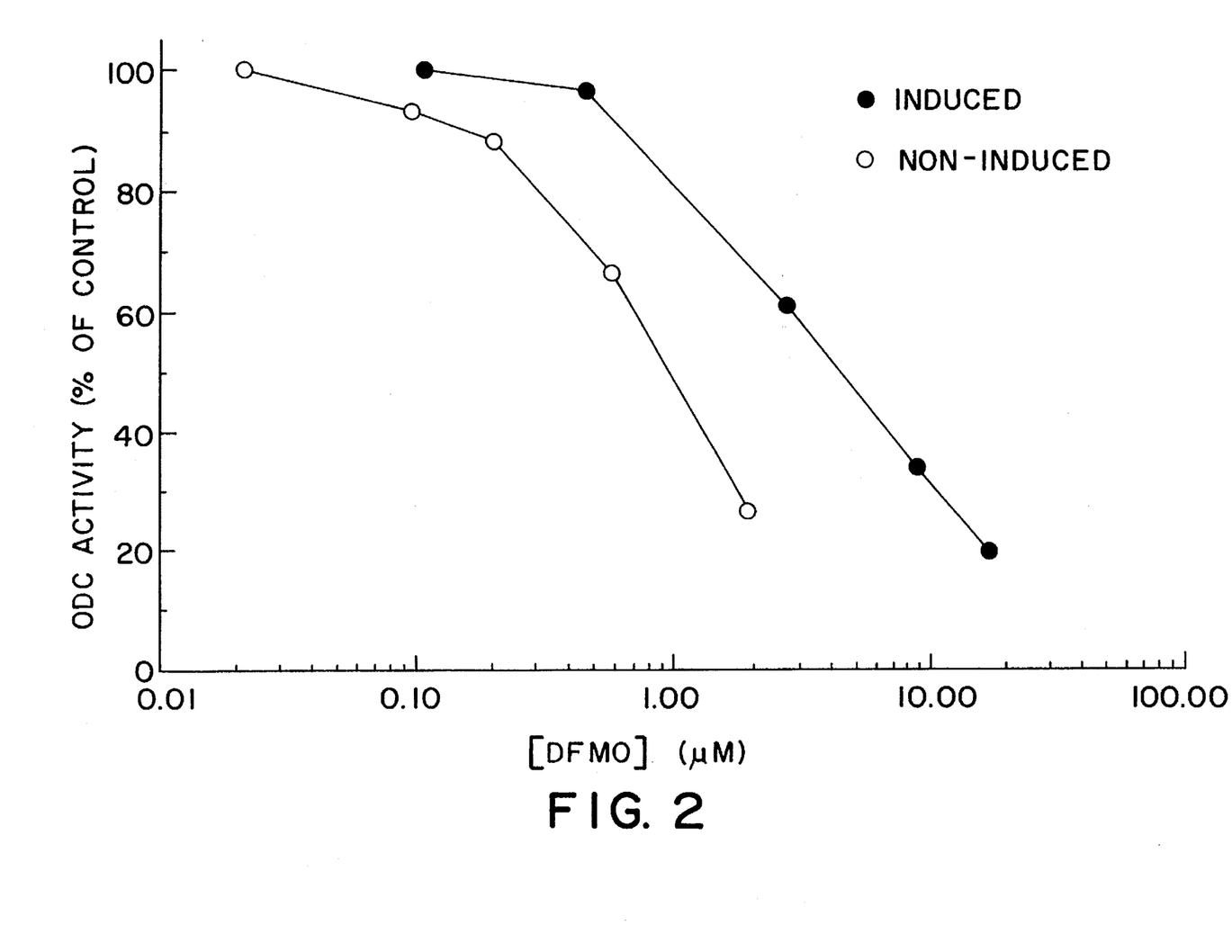
FIG. 2, illustrates the dose-dependent inhibition with difluoromethylornithine of ornithine decarboxylase activity from wild type AA8 cell grown in the absence or presence of fresh serum-containing medium.

The increase in ornithine decarboxylase activity was found to be a result of a parallel increase in the number of ornithine decarboxylase molecules. This was done by a titration of the actual number of catalytically-active ornithine decarboxylase molecules per cell using the irreversible inhibitor DL-o-difluoromethylornithine (DFMO). This substrate-analog is a mechanism-based inhibitor that binds stoichiometrically active ornithine decarboxylase molecules in an irreversible manner. Two crude cytosolic extracts were prepared: one from $2 \times 10^7$ cells of AA8 which received the fresh medium and another without this medium and the ornithine decarboxylase activity was irreversibly inhibited by DFMO. In the attached FIG. 2 is illustrated the dose-dependent inhibition of ornithine decarboxylase activity derived from the serum with the fresh medium (induced) and without said medium (non-induced). As can be noticed, the concentration of DMFO required to reduce the ornithine decarboxylase by 50% (known as $IC_{50}$) for that derived from AA8-induced was 5.0 uM, whereas for that derived from the same number of non-induced AA8 cells it was only 1.1 uM. These results concur with the increase of 4.3 times in the ornithine decarboxylase activity as obtained with induced AA8 cells, as shown in FIG. 1. This result supports the conclusion that the elevation in ornithine decarboxylase activity after addition of the fresh medium is a consequence to a parallel increase in the number of active ornithine decarboxylase molecules.

Figure 3A:
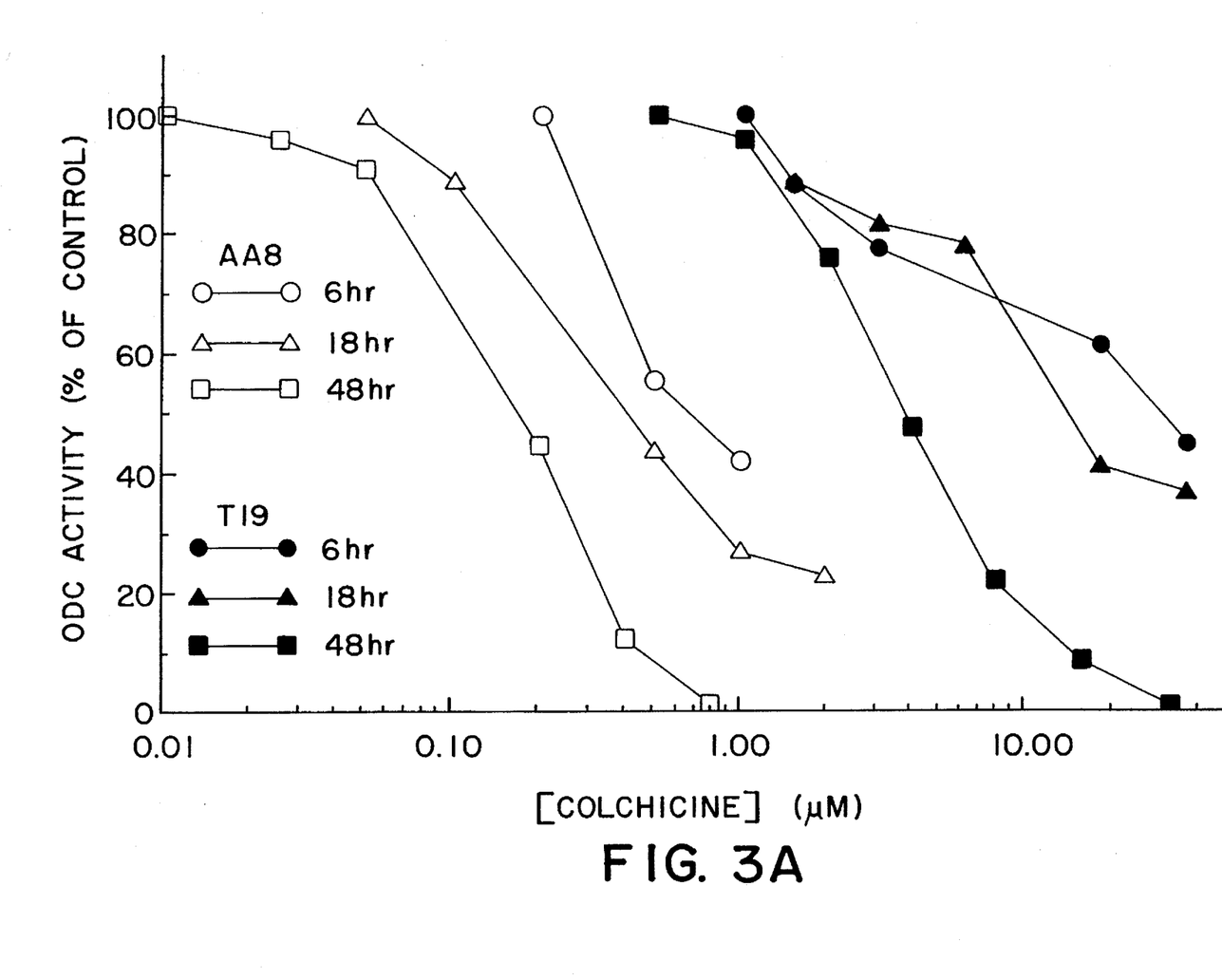
FIG. 3A, illustrates the inhibition of cellular ornithine decarboxylase activity

Based on the above results discovered by the Inventors, further tests were done on the correlation between the ornithine decarboxylase activity and the resistance to cytotoxic agents or cellular sensitivity. Monolayers of parental AA8 and multidrug resistant T19 cells grown for 4 days at 37° C., were exposed to various concentrations of the antimitotic agent colchinine, for 6 hours, 18 hours and 48 hours and then the activity of ornithine decarboxylase was determined. It was found that increased colchinine concentrations, caused a dose-dependent decrease in ornithine decarboxylase activity, both in AA8 and T19 cells. This appears in a clear manner from the attached FIG. 3A. As can be noticed, even a short treatment of only 6 hours with colchinine, was sufficient to detect the sensitivity of AA8 cells and the high level of multi-drug resistance in T19 cells to colchinine.

Figure 3B:
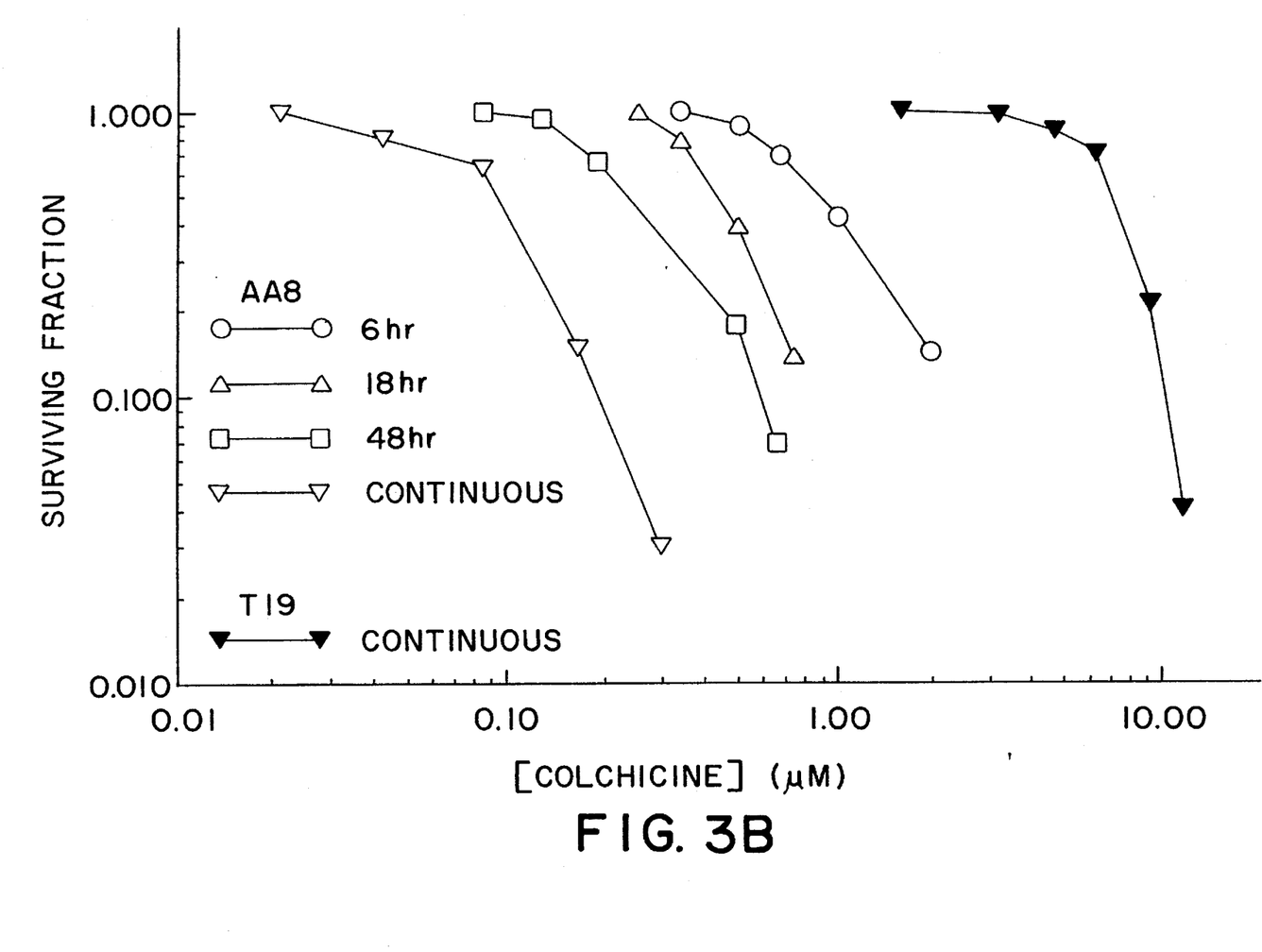
FIG. 3B illustrates clonal survival in AA8 cells following colchicine exposure for various periods of time.

Clonogenic cytotoxic assays were performed with AA8 and T19 cells exposed to various concentrations of colchinine for 6 hours, 18 hours, 48 hours or continuously, and each time the clonal surviving fractions were determined. It was found that the $LD_{50}$ (50% lethal doses) of colchinine to AA8 cells, at the above periods were: 848 nM, 426 nM, 245 nM and 100 nM, respectively, while the $LD_{50}$ for T19 cells treated continuously with colchinine was 6.7 uM, as can be noticed from FIG. 3B. The differences in the $IC_{50}$ values between T19 and AA8 cells reflect correctly the differences in the colchinine resistance levels of T19 cells as compared to parental AA8 cells.

Figure 4:
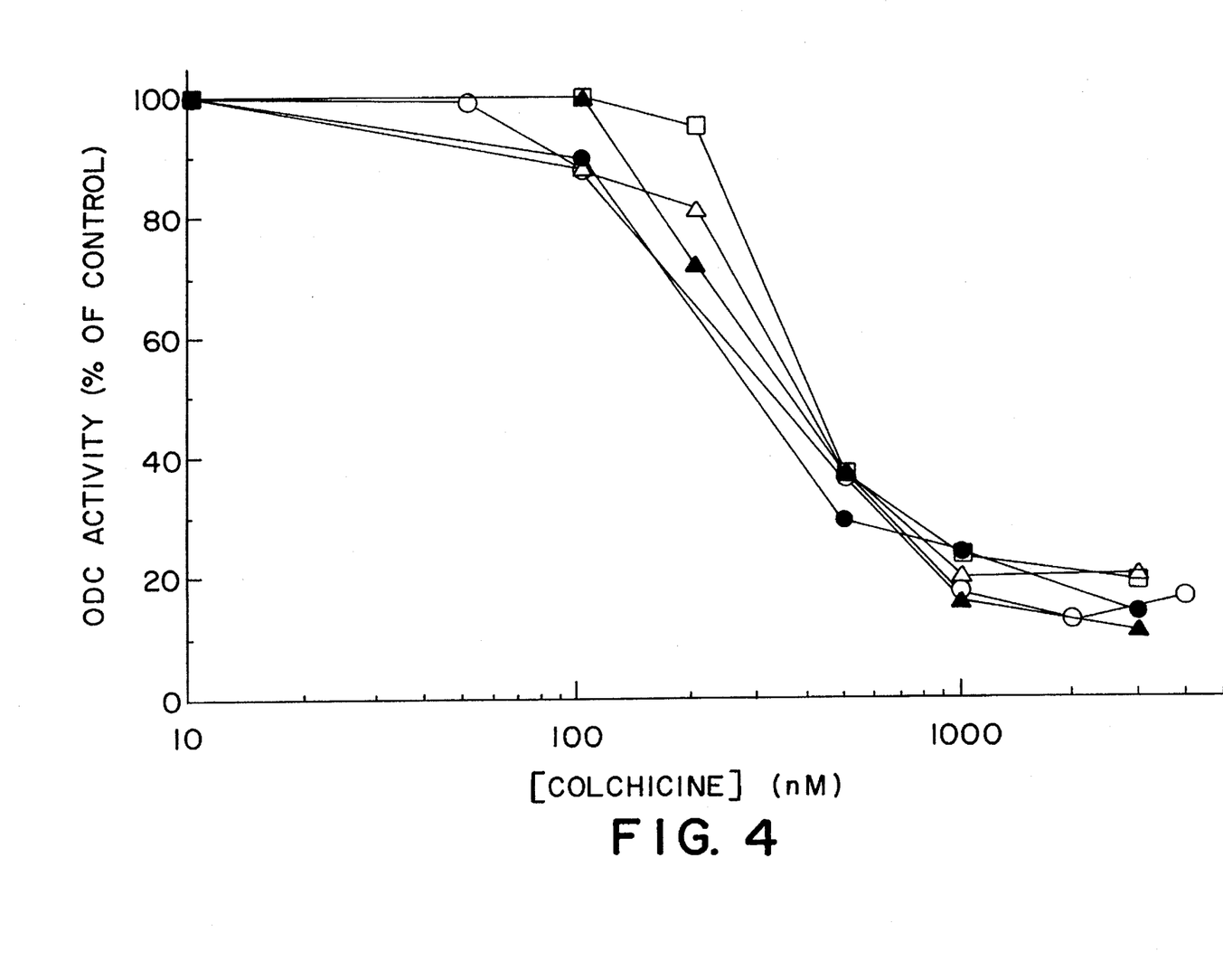
FIG. 4, illustrates the reproducibility of ornithine decarboxylase assay in repeated independent experiments of cellular sensitivity to colchicine.
Figure 5A:
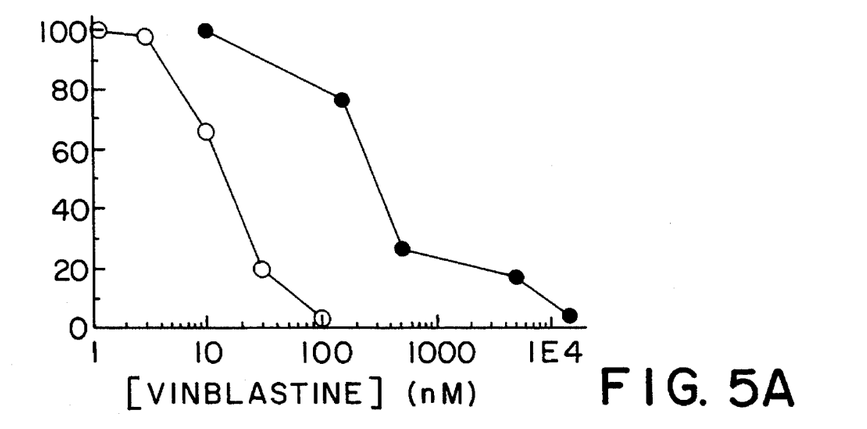
FIG. 5A, through FIG. 5I shows the determination by the ornithine decarboxylase assay of cellular sensitivity and resistance to various anticancer drugs in AA8 and multidrug resistance T19 cells.
Figure 5B:
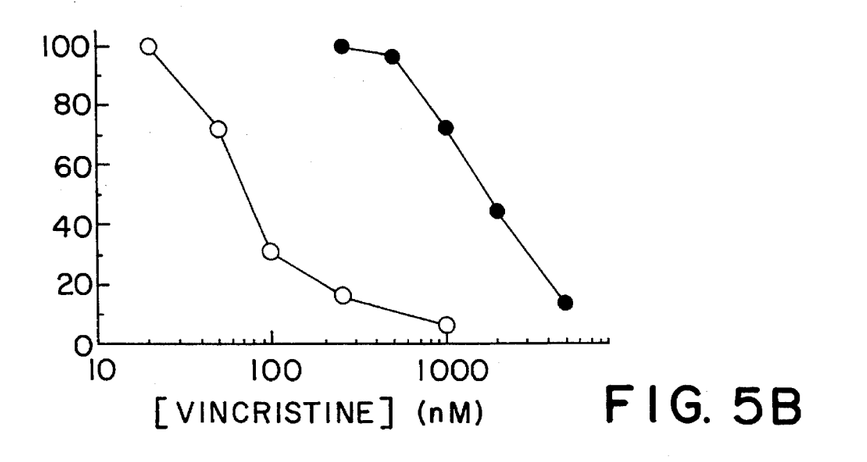
Figure 5C:
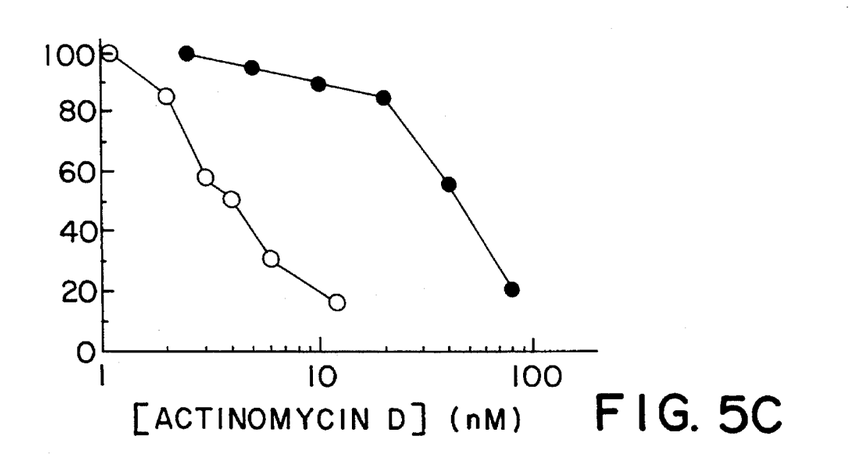
Figure 5D:
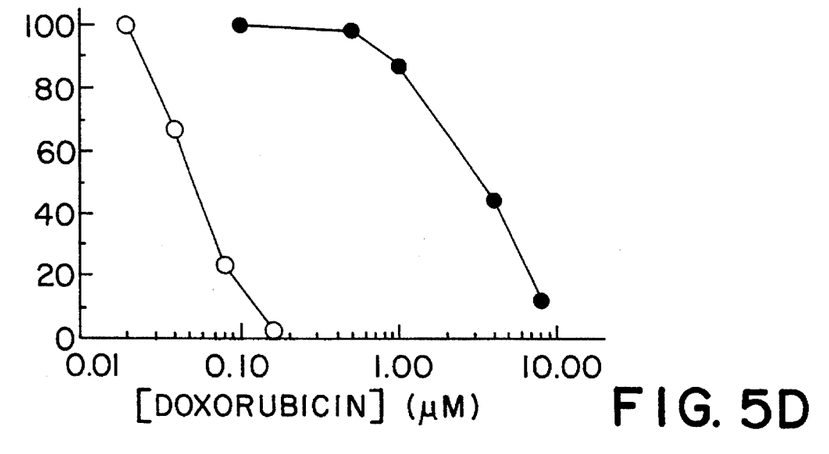
Figure 5E:
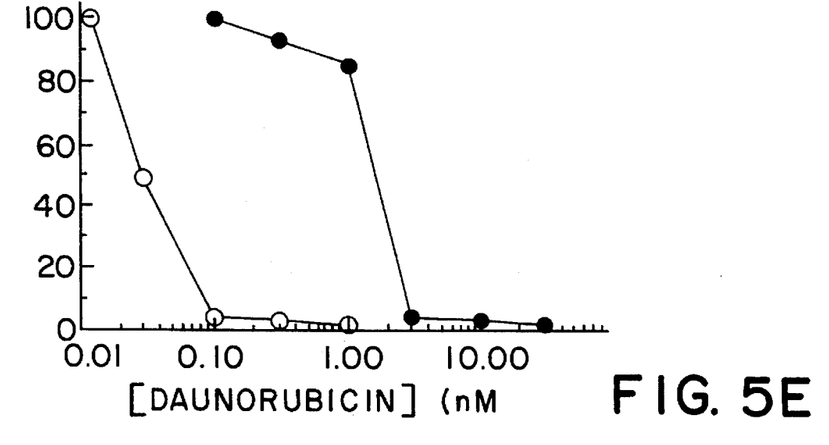
Figure 5F:
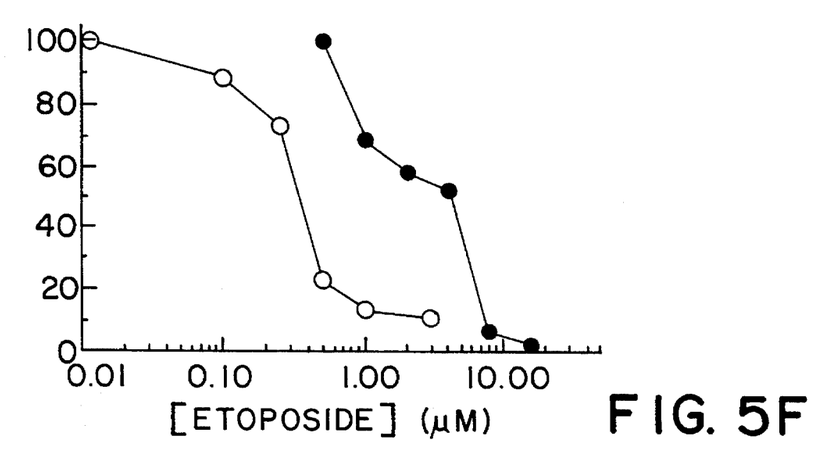
Figure 5G:
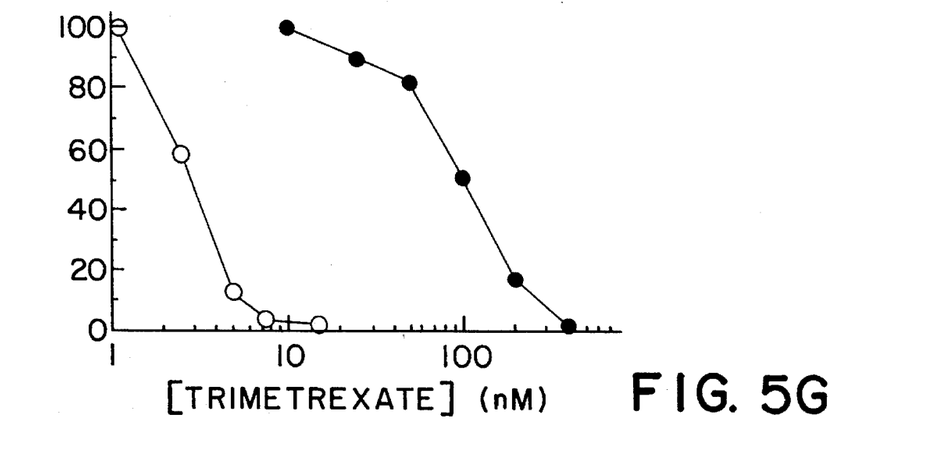
Figure 5H:
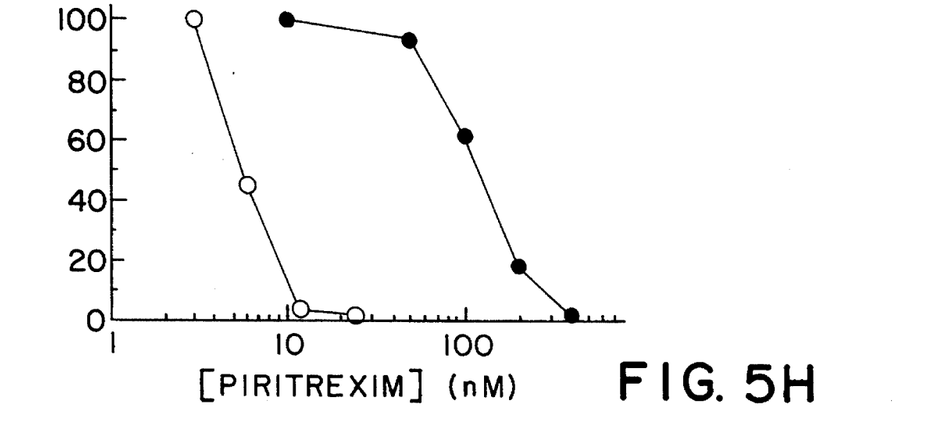
Figure 5I:
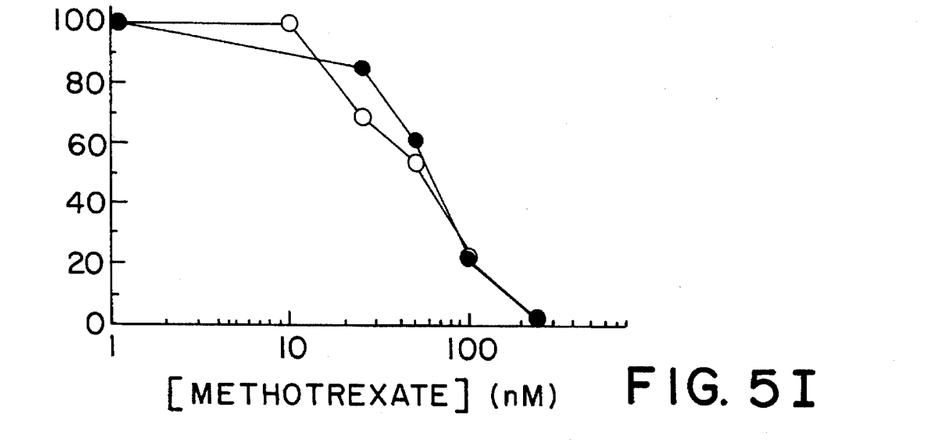

The reproducibility of the ornithine decarboxylase activity assay in the determination of cellular sensitivity to cytotoxic agents was tested by a number of independent experiments with colchinine in parental AA8 cells over a period of 1 year. As appears in FIG. 4, the mean $IC_{50}$ (a reduction of 50% in the ornithine decarboxylase) value obtained with AA8 cells in several independent experiments was 404+8 nM (S.E). Thus, it can be concluded that the ornithine decarboxylase assay displays a high degree of reproducibility in the detection of cellular sensitivity to cytotoxic drugs.

In the same manner, this assay was tested with various anticancer drugs of various structure and distinct mechanisms of action. The following cytotoxic agents were tested: vinca alkaloids, anthracyclines, epipodophyllotoxins, actinomycin D and antifolates. Typical doseresponse curves of decreasing the ornithine decarboxylase activity versus increasing concentrations of some chemotherapeutic agents, are presented in FIG. 5A through FIG. 5I and in the following Table 1.

TABLE I

Sensitivity of wild type AA8 cells and multidrug resistance levels of T19 cells to various cytotoxic agents as determined by the ODC assay and clonogenic method.

| | Incubation Time(hr) | ODC ASSAY | | | CLONOGENIC ASSAY | | |
|---|---|---|---|---|---|---|---|
| | | AA8 | T19 | Resistance (-fold) | AA8 | T19 | Resistance (-fold) |
| Antimetabolites Folic acid analogs | | | | | | | |
| Methotrexate | 48 | 56.5 | 63.8 | 1.1 | 25.1 | 30.6 | 1.2 |
| Trimetrexate | 48 | 2.9 | 72.4 | 25.0 | 2.4 | 68.6 | 28.6 |
| Piritrexim | 48 | 5.8 | 127.3 | 22.0 | 4.6 | 113 | 24.5 |
| Metoprine | 48 | 13.8 | 53.2 | 3.9 | 12.6 | 33.7 | 2.7 |
| Natural Products Vinca alkaloids | | | | | | | |
| Vinblastine | 18 | 15.9 | 275 | 17.3 | 3.0 | 80 | 26.7 |
| Vincristine | 18 | 79.6 | 1534 | 19.2 | 8.2 | 229 | 28.1 |
| Epipodophyllotoxins | | | | | | | |

TABLE I-continued

Sensitivity of wild type AA8 cells and multidrug resistance levels of
T19 cells to various cytotoxic agents as determined by the ODC
assay and clonogenic method.

|  | Incubation Time(hr) | ODC ASSAY | | | CLONOGENIC ASSAY | | |
| --- | --- | --- | --- | --- | --- | --- | --- |
|  |  | AA8 | T19 | Resistance (-fold) | AA8 | T19 | Resistance (-fold) |
| Etoposide | 48 | 366 | 4176 | 11.4 | 265 | 4200 | 15.9 |
| Antibiotics |  |  |  |  |  |  |  |
| Actinomycin D | 18 | 3.7 | 42 | 11.3 | 2.2 | 49.7 | 22.6 |
| Doxorubicin | 48 | 55 | 3581 | 65.0 | 40 | 8450 | 61.3 |
| Daunorubicin | 48 | 29.6 | 1864 | 63.0 | 8.6 | 726 | 84.1 |
| Miscellaneous |  |  |  |  |  |  |  |
| Puromycin | 48 | 10.5 | 315 | 30.0 | 4.5 | 116 | 25.8 |
| Colchicine | 18 | 404 | 13800 | 34.2 | 100 | 6700 | 67.0 | a-Numbers represent mean $LD_{50}$ (clonogenic assay) or $IC_{50}$ (ODC assay) values (in nM) obtained from two to four independent experiments.

As can be noticed from the above Table 1 and FIG. 5A through FIG. 5I the resistance of T19 cells is clearly reflected in the markedly increased anticancer drug concentrations required to reduce the ornithine decarboxylase activity. The resistance of T19 cells was clearly supported by the significant increase of anticancer drug concentrations which were required to reduce the ornithine decarboxylase activity.

Figure 6A:
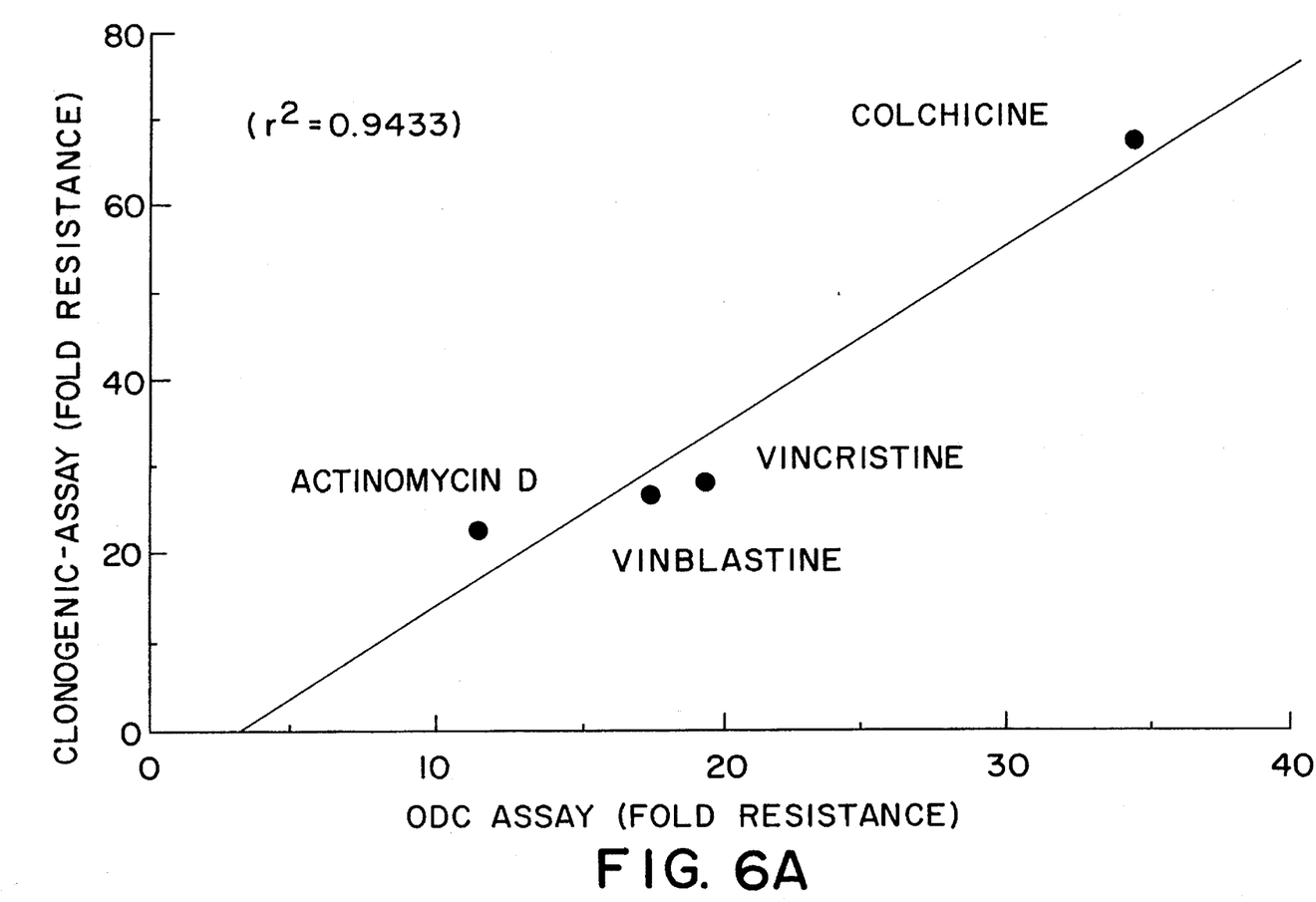
FIG. 6A and FIG. 6B illustrate the correlation of anticancer drug resistance levels determined by the clonogenic assay versus resistance levels obtained by the ornithine decarboxylase assay (FIG. 6A after 8 hours and FIG. 6B after 48 hours).
Figure 6B:
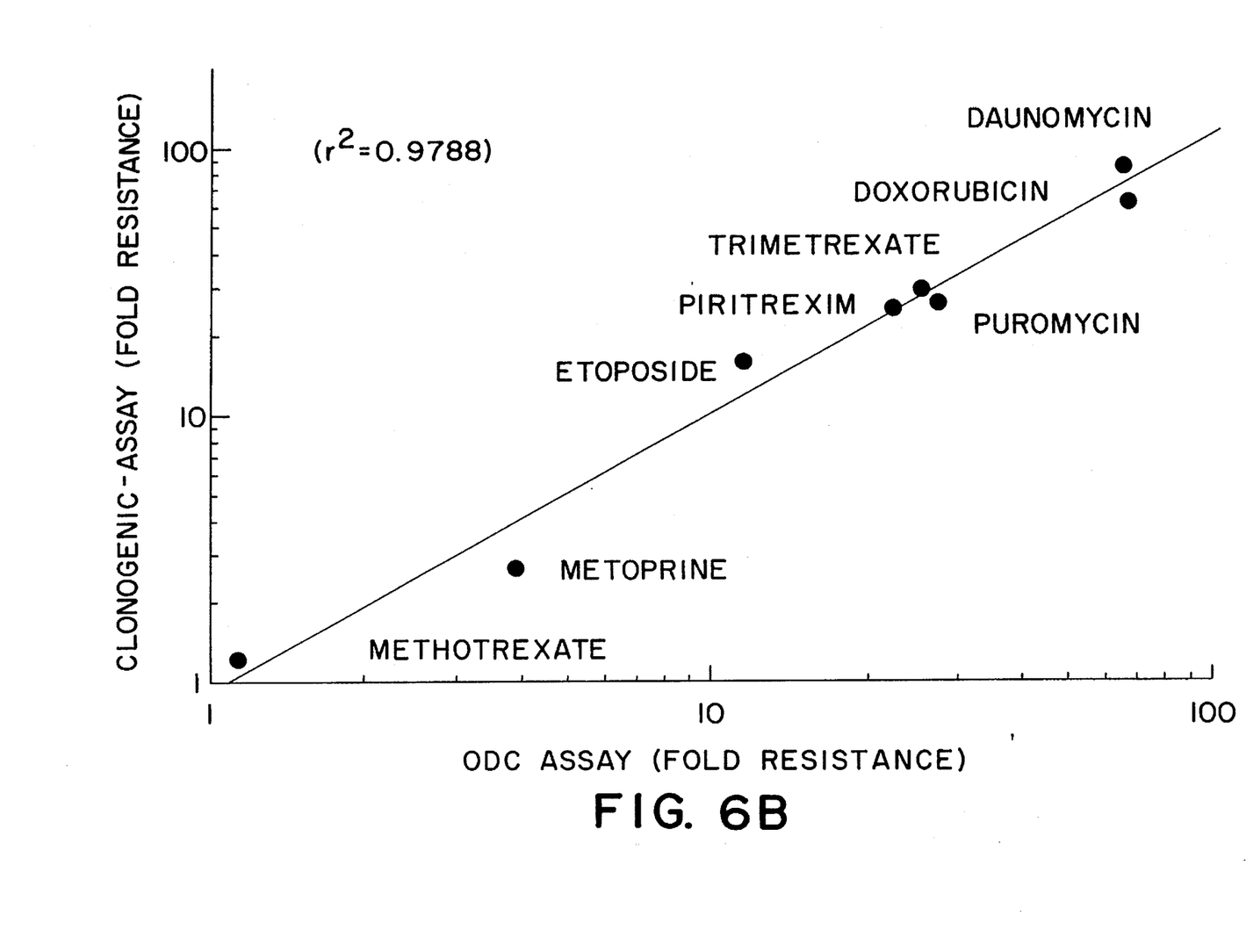

According to another aspect of the present invention, the ornithine decarboxylase activity is suitable for the prediction of cellular resistance to antineoplastic agents. The degree of drug resistance in T19 cells obtained by the well-established cytotoxic clonogenic assay was plotted versus the T19/AA8 ratio of $IC_{50}$ values obtained with the ornithine decarboxylase assay when using various anticancer drugs. As appears in the attached FIG. 6A, and FIG. 6B the anticancer drug resistance levels of T19 obtained with the clonogenic assay, correlate well, $r^2=0.943$ for a drug exposure time of 18 hours (FIG. 6A) and $r^2=0.979$ for a drug exposure of 48 hours (FIG. 6B).

Figure 7A:
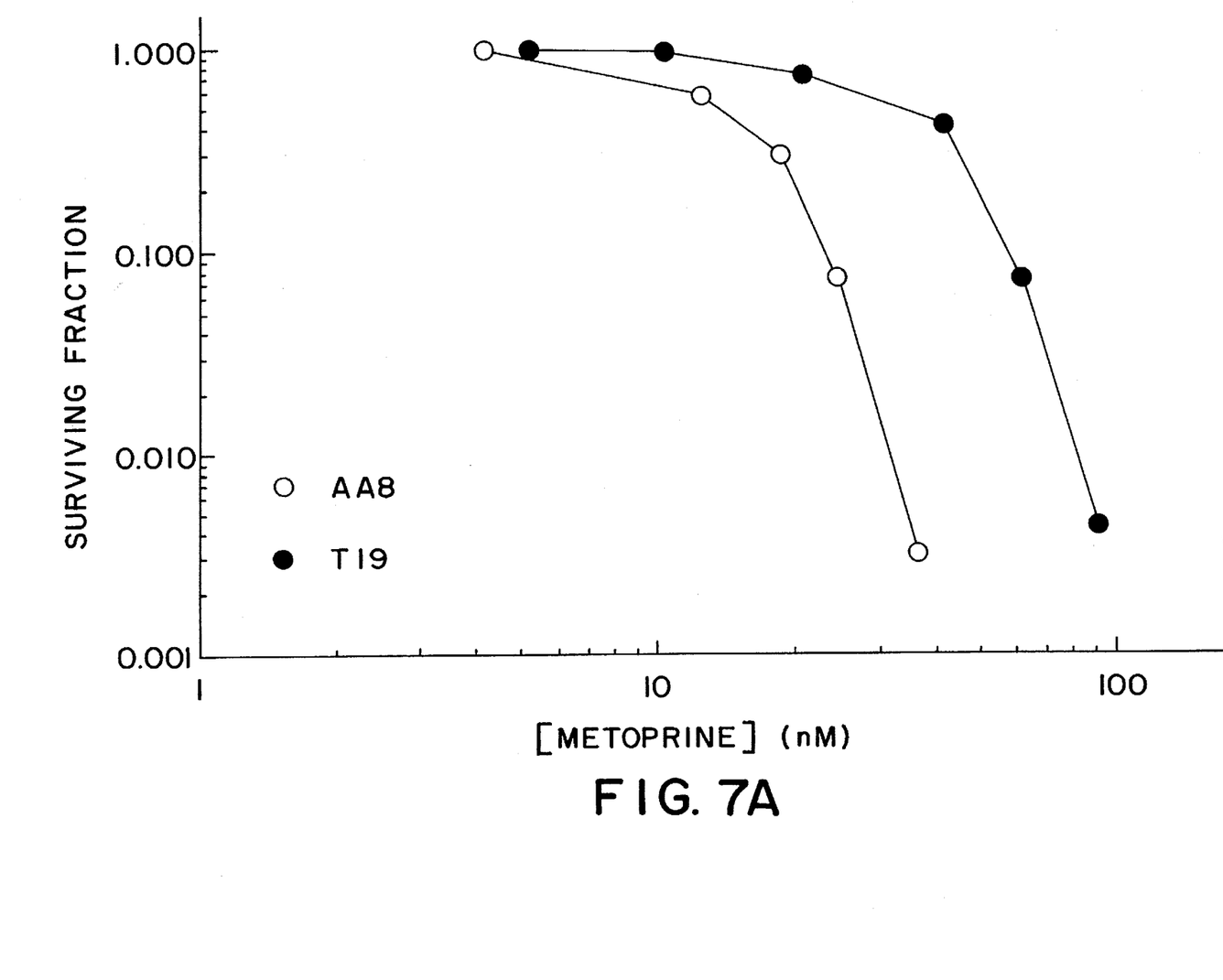
FIG. 7A and 7B illustrate the sensitivity of the ornithine decarboxylase activity assay in detection of low levels of cellular resistance to the antifolate metoprine as compared to the clonogenic assay (FIG. 7A after 8 days and FIG. 7B after 48 hours).
Figure 7B:
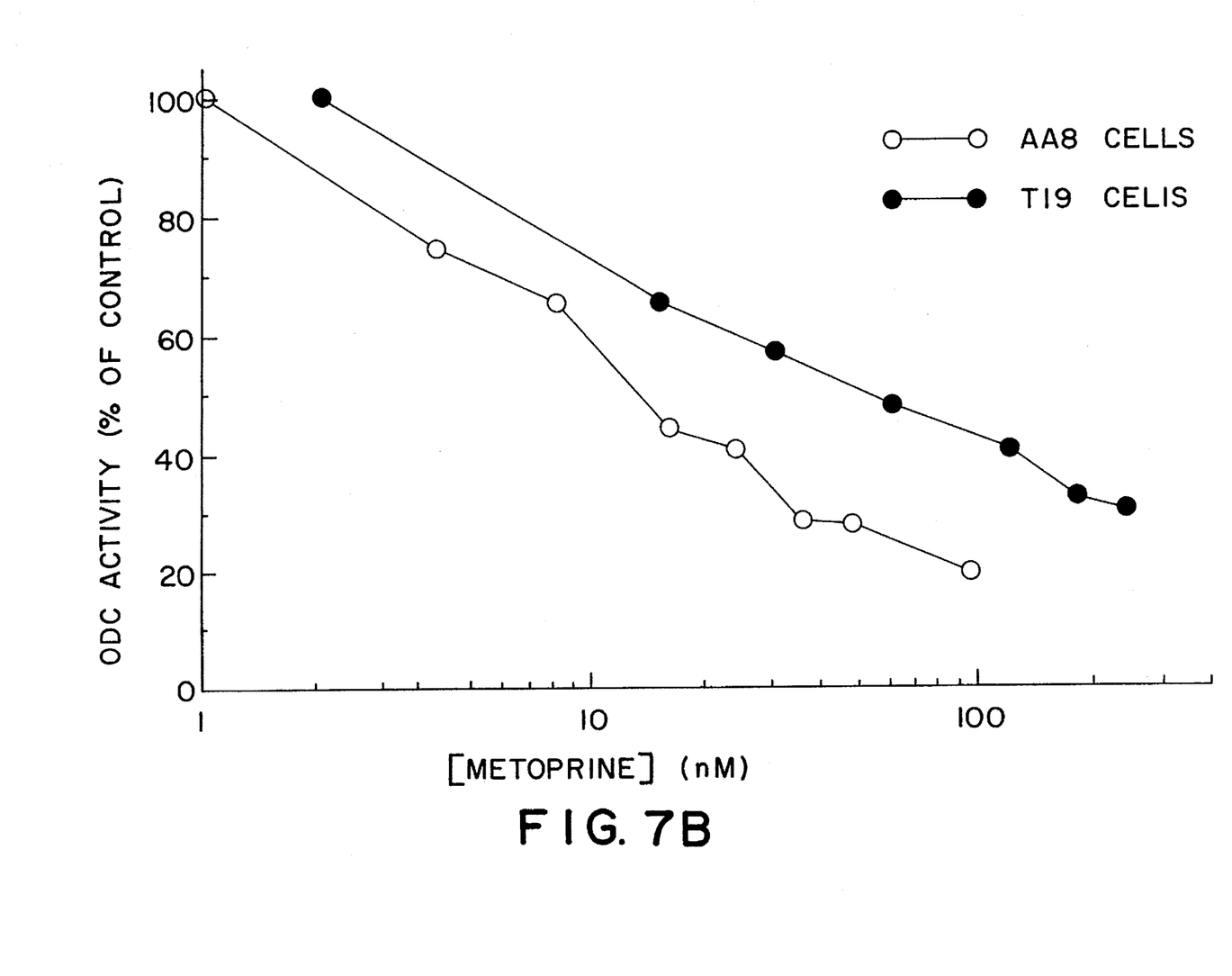

The sensitivity of the enzymatic assay according to the present invention was also confirmed. Using a clonogenic cytotoxic assay, a low level of 2.7-fold resistance to the lipid-soluble antifolate metoprine was obtained in. multidrug resistant T19 cells as compared to their parental AA8 cells (FIG. 7A). By carrying out the ornithine decarboxylase assay on cytosolic extracts derived from AA8 and T19 cells treated for 48 hours with various metoprine concentrations, it was found that T19 cells displayed a 3.9-fold resistance to metoprine when compared to parental AA8 cells (FIG. 7B). This means, that as little as 2.7- to 3.9-fold of cellular resistance to cytotoxic agents could be reliable monitored with the ornithine decarboxylase activity assay according to the present invention.

The rise in the activity of ornithine decarboxylase after adding a serum containing medium to quiescent mammalian cells may be determined by any sensitive immunological technique known in the art, such as ELISA, radioimmunoassay, immunofluorescence, fluorescence microscopy and flow cytometry. In particular preferably will be the ELISA technique, which is now frequently used in many clinical laboratories. The flow cytometry analysis of malignant cells stained with fluorescent antibodies directed to human ornithine decarboxylase, may detect elevated-levels of ornithine decarboxylase in individual cells, thus minimizing the number of cells to $10^3$ as required for a reliable flow cytometric analysis as compared to the two orders of magnitude higher cell number generally used for ornithine decarboxylase activity assay.

The assay for the identification and determination of multidrug resistance according to the present invention, is characterized by a number of beneficial characteristics over the currently used chemosensitivity methods. Among the main important advantages the following are mentioned versatility, sensitivity, reproducibility, reliability, rapidity, simplicity and independence of clonogenicity.

The versatility is a very important advantage, since the assay is equality efficient in monitoring cellular sensitivity or resistance to a wide-spectrum of anticancer drugs of dissimilar structure and of diverse mechanisms of action, thus being not restricted to a certain group of antineoplastic agents.

While the invention has been described in respect to some embodiments and specific examples of anticancer drugs, it should be understood that a person skilled in the art, after reading the present specification may insert some modifications, or using other drugs then those specified in the specification, without being outside the scope of the invention as covered by the appended claims.

We claim:

1. A rapid method for assessing sensitivity or resistance of mammalian cells of unknown drug sensitivity to an anticancer agent, which comprises the steps of:

(a) separately incubating quiescent mammalian cells of unknown drug sensitivity and quiescent mammalian cells of known drug sensitivity in medium containing a growth stimulant in an amount sufficient to increase the level or ornithine decarboxylase protein in the cells, and determining the levels of ornithine decarboxylase protein in the cells by an immunological technique, thereby determining the levels of ornithine decarboxylase activity;

(b) repeating step (a) in the presence of various concentrations of the anticancer agent; and (c) determining the level of drug sensitivity or resistance of the mammalian cells of unknown drug sensitivity by determining the ratio of the concentration of the anticancer agent required to reduce the ornithine decarboxylase activity level of the cells of unknown drug sensitivity by 50% ($IC_{50}$) to the concentration of the anticancer drug required to reduce the ornithine decarboxylase activity level of the cells of known sensitivity by 50% ($IC_{50}$).

2. The method according to claim 1, wherein said growth stimulant comprises hormones, growth factors, hormones and growth factors, or serum.

3. The method according to claim 1, wherein the levels of ornithine decarboxylase protein are determined by an immunological technique selected from the group consisting of ELISA, radioimmunoassay, immunofluorescence, flow cytometry and fluorescence microscopy.

4. The method according to claim 1, wherein the levels of ornithine decarboxylase protein in the cells are determined by titration of the actual number of catalytically active ornithine decarboxylase molecules per cell.

5. The method according to claim 4 wherein the titration is carried out by determining the concentration of ornithine decarboxylase inhibitor DL-O=difluoromethylornithine (DFMO) required to reduce the ornithine decarboxylase activity by 50%.

6. The method according to claim 1 wherein the anticancer agent is selected from the group consisting of vinca alkaloids, anthracyclines, epipodophyllotoxins, actinomycin D and anti-folates.

7. The method according to claim 1, wherein the levels of ornithine decarboxylase protein are determined from a crude cytosolic extract of the cells.

8. The method according to claim 7, wherein optimal ornithine decarboxylase levels for measuring are achieved by varying the volume of the crude cytosolic extract.

9. The method according to claim 1, wherein the mammalian cells of unknown drug sensitivity are primary cell isolates or cell lines.

10. The method according to claim 1, wherein the mammalian cells are tumor cells.

11. The method according to claim 1, wherein the mammalian cells are malignant cells from the central nervous system, colon, lung, liver, kidney, ovary, breast, a melanoma or a leukemia.

12. The method according to claim 1, wherein the mammalian cells of known drug sensitivity are primary cell isolates or cell lines.

13. The method according to claim 1, wherein the mammalian cells of known drug sensitivity are normal cells or malignant cells.

* * * * *